(12) United States Patent
Jimbo et al.

(10) Patent No.: US 6,372,871 B1
(45) Date of Patent: Apr. 16, 2002

(54) DITHIOCARBONATE COMPOSITION

(75) Inventors: Shinichiro Jimbo; Shoshiro Matsushita, both of Tokyo; Ikuo Shimizu, Yokkaichi; Iwao Hotta, Yokkaichi; Masanori Ikuta, Yokkaichi; Izumi Itani, Yokkaichi, all of (JP)

(73) Assignee: Kyowa Yuka Co., Ltd., Tokyo (JP)

( * ) Notice: Subject to any disclaimer, the term of this patent is extended or adjusted under 35 U.S.C. 154(b) by 0 days.

(21) Appl. No.: 09/319,449
(22) PCT Filed: Nov. 21, 1997
(86) PCT No.: PCT/JP97/04258
  § 371 Date: Jun. 4, 1999
  § 102(e) Date: Jun. 4, 1999
(87) PCT Pub. No.: WO98/24849
  PCT Pub. Date: Jun. 11, 1998

(30) Foreign Application Priority Data

Apr. 12, 1996 (JP) ................................. 8-323939

(51) Int. Cl.$^7$ ................................. C08F 28/06
(52) U.S. Cl. ................. 526/257; 524/547; 549/30
(58) Field of Search .............. 526/257; 524/547; 549/30

(56) References Cited

FOREIGN PATENT DOCUMENTS

| JP | 5-247027 | 9/1993 |
| JP | 7-62190 | 3/1995 |
| JP | 7-145164 | 6/1995 |
| JP | 8-217774 | 8/1996 |
| JP | 9-59324 | 3/1997 |

*Primary Examiner*—Bernard Lipman
(74) *Attorney, Agent, or Firm*—Fitzpatrick, Cella, Harper & Scinto

(57) ABSTRACT

The present invention provides a composition comprising a polymer or a compound having at least one 5-membered ring dithiocarbonate group represented by general formula (I):

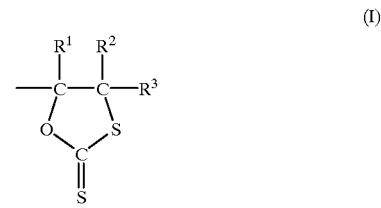

(wherein, in the formula, $R^1$, $R^2$, and $R^3$ are the same or different, each of which denotes hydrogen or a lower alkyl), and a ketimine derivative, an enamine derivative, or an aldimine derivative. The composition is useful in coatings, adhesives, inks, sealing agents, sealants, and the like.

12 Claims, No Drawings

DITHIOCARBONATE COMPOSITION

TECHNICAL FIELD

The present invention relates to dithiocarbonate compositions which are useful in coatings, adhesives, inks, sealing agents for building use, sealants for semiconductors, and the like.

BACKGROUND ART

A reactive polymer or compound which has functional groups in its molecules has various uses. For example, if a composition containing such a polymer or a compound is used as an active ingredient for a coating, an adhesive, an ink, a sealing agent for building use, a sealant for semiconductors or the like, such physical properties as hardness, strength, adhesion, water resistance, chemical resistance, heat resistance, and the like can be improved by allowing cross-linking reactions to occur under specific conditions after application or printing of the composition.

Japanese Unexamined Patent Application, First Publication No. Hei 5-247027 discloses a homopolymer of 5-(methacryloyl)methyl-1,3-oxathiolane-2-thione (MOT) as a polymer having 5-membered dithiocarbonate groups; however, this publication does not disclose a detailed method of polymerization, values expressing physical properties before and after cross-linking reaction, or usefulness of the polymer.

The "Journal of Polymer Science., Part A: Polymer Chemistry" 33, 1005 (1995), discloses a composition comprising a vinyl copolymer having 5-membered ring dithiocarbonate groups and an amine compound. However, since the 5-membered ring dithiocarbonate groups are highly reactive with the amine compound in this composition, this composition cannot be used as a one-liquid type composition for use in a coating or an adhesive, but this composition must be used as a two-liquid type composition in which mixing is performed immediately before use.

Japanese Unexamined Patent Application, First Publication No. Hei 7-145164 discloses a process for cross-linking a compound having 5-membered ring dithiocarbonate groups and a polymer having functional groups containing active hydrogens. Japanese Unexamined Patent Application, First Publication No. Hei 5-247027 describes a composition comprising a compound having 5-membered ring dithiocarbonate groups and a nucleophile. Japanese Unexamined Patent Application, First Publication No. 7-62190 discloses an aqueous polymer composition comprising a vinyl copolymer containing 5-membered ring dithiocarbonate groups and a compound having two or more amino groups or imino groups; however, a combination with a ketimine derivative, an enamine derivative, or an aldimine derivative is not disclosed. It is difficult to use the compositions described in these publications as a one-liquid type coating or adhesive for the reasons described above.

DISCLOSURE OF INVENTION

The present invention provides a composition comprising a polymer or a compound having at least one 5-membered ring dithiocarbonate group represented by general formula (I):

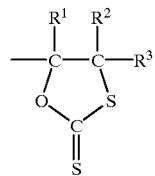

(wherein, in the formula, $R^1$, $R^2$, and $R^3$ are the same or different, each of which denotes hydrogen or a lower alkyl), and a ketimine derivative, an enamine derivative, or an aldimine derivative.

In the descriptions of the general formulae of the present invention, "lower alkyl" means a C1 to C4 straight or branched alkali such as methyl, ethyl, propyl, isopropyl, butyl, isobutyl, sec-butyl, and t-butyl.

Examples of the polymer having at least one 5-membered ring dithiocarbonate group represented by general formula (I) are a vinyl polymer, a polyester resin, an alkyd resin, a polyamide resin, a polyether resin, a polyurethane resin, and a copolymer in which these compounds are chemically bonded to each other. Among these, a vinyl polymer is preferable, and a vinyl copolymer containing a structural unit represented by general formula (II)

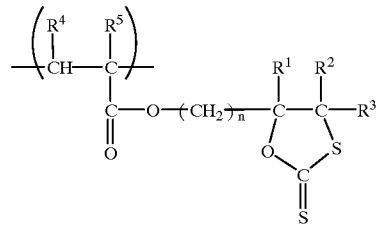

(wherein, in the formula, the definitions of $R^1$, $R^2$, and $R^3$ are the same as those above, $R^4$ and $R^5$ are the same or different, each of which denotes hydrogen, methyl, or ethyl, and n denotes an integer of 1 to 4) is more preferable.

The vinyl copolymer having at least one 5-membered ring dithiocarbonate group contains a structural unit having a 5-membered ring dithiocarbonate group and 1 to 10 types of structural units other than the structural unit having a 5-membered ring dithiocarbonate group.

Examples of the vinyl monomer other than the monomer having a 5-membered ring dithiocarbonate group, which is a material for the vinyl copolymer having at least one 5-membered ring dithiocarbonate group, to be copolymerized with the monomer having a 5-membered ring dithiocarbonate group are (meth)acrylic acid, maleic acid, fumaric acid, itaconic acid, crotonic acid, monoethyl maleate, monomethyl itaconate, methyl (meth)acrylate, ethyl (meth) acrylate, butyl (meth)acrylate, isobutyl (meth)acrylate, t-butyl (meth)acrylate, 2-ethylhexyl (meth)acrylate, lauryl (meth)acrylate, styrene, vinyltoluene, α-methylstyrene, dimethylstyrene, divinylbenzene, N-methylol(meth) acrylamide, (meth)acrylamide, (meth)acrylonitrile, vinyl acetate, vinyl propionate, vinyl versate, monoethyl maleate, monobutyl maleate, diethyl maleate, dibutyl maleate, diethyl fumarate, dibutyl fumarate, diethyl itaconate, 2-hydroxyethyl (meth)acrylate, 2-hydroxypropyl (meth)

acrylate, polyethylene glycol mono(meth)acrylate, polypropylene glycol mono(meth)acrylate, dimethylaminoethyl (meth)acrylate, glycidyl (meth)acrylate, dimethylaminoethyl (meth)acrylate, diethylaminoethyl (meth)acrylate, methyl vinyl ether, ethyl vinyl ether, butyl vinyl ether, allyl alcohol, allyl alcohol ester, vinyl chloride, vinylidene chloride, fluoroethylene, and chlorofluoroethylene, butadiene. Among these compounds, acrylic acid or methacrylic acid or a lower alkyl ester such as (meth)acrylic acid, methyl (meth)acrylate, ethyl (meth)acrylate, butyl (meth)acrylate, isobutyl (meth)acrylate, and t-butyl (meth)acrylate can be preferably used. Alternatively, a copolymer of a vinyl monomer and a non-vinyl monomer can be used. Such a copolymer can be produced in accordance with a method for producing a vinyl-modified epoxy resin (Japanese Unexamined Patent Application, First Publication No. Sho 54-30249), a vinyl-modified polyester resin (Japanese Unexamined Patent Application, First Publication No. Hei 1-129072), a vinyl-modified alkyd resin, a vinyl-modified urethane resin (Japanese Unexamined Patent Application, First Publication No. Hei 1-301761), or the like.

In the polymer having at least one 5-membered ring dithiocarbonate group, the content of the structural unit having the 5-membered ring dithiocarbonate group (based on monomer) is preferably 0.2 to 90 mol %.

The molecular weight of the polymer having at least one 5-membered ring dithiocarbonate group is not particularly limited; however, when the polymer is used for a solvent-based coating, one having a weight-average molecular weight of 1,000 to 400,000 can be used, and particularly one having a weight-average molecular weight of 5,000 to 200,000 can be preferably used.

Processes for producing the polymer having at least one 5-membered ring dithiocarbonate group will be explained in the following.

The polymer having at least one 5-membered ring dithiocarbonate group can be obtained by conducting polymerization/polycondensation with a corresponding monomer according to a known method. The monomer having at least one 5-membered ring dithiocarbonate group can be obtained by allowing an oxirane compound and carbon disulfide to react in the presence of alkali halide in accordance with, for example, a known method (Japanese Unexamined Patent Application, First Publication No. Hei 5-257027 or the Journal of Organic Chemistry (J. Org. Chem.), 60, 473 (1995)).

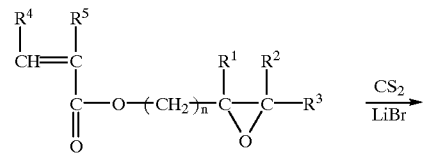

-continued

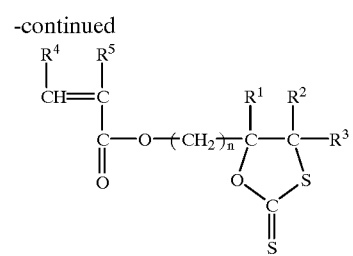

(In the formula, the definitions of $R^1$, $R^2$, $R^3$, $R^4$, $R^5$, and n are the same as those above.)

Alternatively, the polymer having at least one 5-membered ring dithiocarbonate group can also be produced by obtaining a polymer having a functional group (such as a carboxyl group, a hydroxyl group, or an amino group) in advance, and then allowing a bonding reaction to occur with a 5-membered ring dithiocarbonate compound so that it becomes pendent from the polymer.

Examples of processes for producing a copolymer include: a process in which a monomer having a 5-membered ring dithiocarbonate group in the molecule and another copolymerizable monomer are allowed to react; a process in which a homopolymer or a copolymer is synthesized, and thereafter it is graft-copolymerized with another monomer; a process in which after synthesis of a copolymer, polymers are block-copolymerized; and the like.

The polymerization reaction is carried out, for example, in the case of radical polymerization of a vinyl monomer, at 0 to 150° C., or preferably 40 to 120° C., for 1 to 24 hours in the presence of a polymerization initiator at 0.5 to 5 mol % with respect to the amount of the monomer.

If an aqueous emulsified vinyl polymer is desired, a monomer can be subjected to emulsion polymerization in water using an emulsifier and a polymerization initiator according to a known process (Japanese Unexamined Patent Application, First Publication No. Sho 54-110248, or Japanese Examined Patent Application, Second Publication No. Sho 58-20991).

Storage stability of the polymer having at least one 5-membered ring dithiocarbonate group can be improved by making the polymer in a core-shell structure. An emulsion polymer in water of a core-shell type can be synthesized according to a known process (Japanese Unexamined Patent Application, First Publication No. Sho 57-3850, Japanese Unexamined Patent Application, First Publication No. Sho 61-136501, and Japanese Unexamined Patent Application, First Publication No. Hei 5-70733)

The polymer having at least one 5-membered ring dithiocarbonate group can be emulsified in water according to a known process.

As the polymerization solvent, although it varies depending on the polymerization type, in the case of radical polymerization, for example, benzene, toluene, xylene, hexane, cyclohexane, ethyl acetate, butyl acetate, 3-methyl-3-methoxybutyl acetate, acetone, methyl ethyl ketone, methyl isobutyl ketone, diisobutyl ketone, cyclohexanone, methanol, ethanol, propanol, isopropanol, butanol, N-methylpyrrolidone, tetrahydrofuran, acetonitrile, methoxybutanol, methoxybutyl acetate, 3-methyl-3-methoxybutanol, ethylene glycol monobutyl ether, ethylene glycol monobutyl ether acetate, diethylene glycol monobutyl ether, diethylene glycol monobutyl ether acetate, propylene glycol monomethyl ether, dipropylene glycol monomethyl ether, propylene glycol monoethyl ether, propylene glycol monomethyl ether acetate, dipropylene glycol monomethyl ether acetate, 3-methyl-3-methoxy-1-butyl acetate, water, dimethylformamide, dimethylacetamide, or dimethyl sulfoxide can be used As the initiator, although it varies depending on the polymerization type, in the case of radical polymerization, for example, 2,2'-azobisisobutyronitrile, 2,2'-azobis-2-methylbutyronitrile, 2,2'-azobisvaleronitrile, benzoyl peroxide, acetyl peroxide, lauroyl peroxide, 1,1-bis(t-butyl peroxy)-3,3,5-trimethylcyclohexane, t-butyl peroxy-2-ethylhexanoate, cumene hydroperoxide, t-butyl peroxybenzoate, t-butyl peroxide, methyl ethyl ketone peroxide, or m-chloroperbenzoate can be used.

As an emulsifier for aqueous emulsion polymerization, an anionic emulsifier such as an alkylbenzenesulfonate salt, a nonionic emulsifier such as polyethylene glycol alkyl phenyl ether, a reactive emulsifier such as "ELEMINOL JS-2" (a product of Sanyo Chemical Industries, Ltd.), or a polymer emulsifier in which a hydrophilic group such as a salt of a carboxyl group, a salt of a sulfonic group, or the like is introduced to a polymer of various types such as a vinyl polymer or a polyester polymer can be used.

In addition, one of various protective colloids for stabilized emulsification such as polyvinyl alcohol and cellulose can be incorporated.

In order to obtain an aqueous emulsion dispersion composition by a method other than aqueous emulsion polymerization, a self-emulsification method in which a copolymer having a tertiary amine salt of a carboxyl group introduced into its molecule is used, or an emulsification method in which an external emulsifier is used may be employed.

Instead of the above production methods, the polymer of the present invention can also be obtained by allowing a polymer having an oxirane structure to react with carbon disulfide in the presence of alkali halide such as lithium bromide in accordance with a known method (Japanese Unexamined Patent Application, First Publication No. Hei 5-247027; the Journal of Organic Chemistry (J. Org. Chem.), 60, 473 (1995)).

In order to chemically bond the vinyl polymer and the polyester resin, a method in which a vinyl polymer having a functional group such as a carboxyl group, a hydroxyl group, and a glycidyl group and a polyester resin having a glycidyl group, a hydroxyl group, a carboxyl group, or the like, are synthesized in adivance, and thereafter the vinyl polymer and the polyester resin are bonded by esterification (Japanese Unexamined Patent Application, First Publication No. Hei 1-129072), or a method in which an unsaturated polyester resin having a radical polymerizable functional group (a vinyl group or a conjugated double bond) is synthesized, and thereafter a vinyl monomer is grafted thereto by radical polymerization may be employed. Examples of a compound having at least one 5-membered ring dithiocarbonate group according to the present invention are a dithiocarbonate compound derived from a phenol, a dithiocarbonate compound derived from an alcohol, a dithiocarbonate compound derived from a carboxylic acid, and a compound obtained by allowing an oxirane compound such as diphenyl epoxy resin, etylene oxide, propylene oxide, butylene oxide, triglycidyl isocyanurate, epoxidated soybean oil, and an epoxidated fatty acid of soybean oil to react with carbon disulfide.

Examples of the dithiocarbonate compound derived from a phenol are compounds obtained by preparing a glycidyl ether by allowing a phenol compound, such as phenol, resorcin, hydroquinone, catechol, cresol novolac, and novolac, to react with epichlorohydrin, and then allowing the glycidyl ether to react with carbon disulfide. Among these examples, a hydroxy compound having a thiocarbonate group represented by general formula (III) can be preferably used:

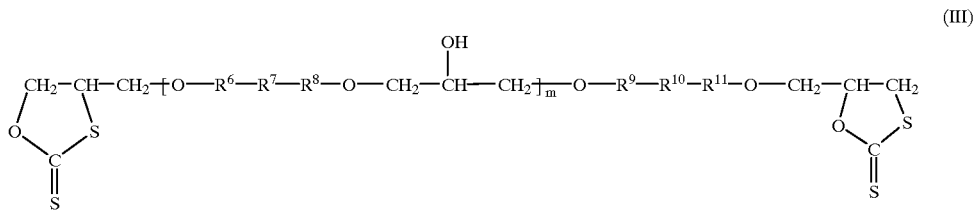

(III)

(wherein, in the formula, $R^6$, $R^8$, $R^9$, and $R^{11}$ are the same or different, each of which denotes phenylene in which 1 to 4 hydrogen atoms may be substituted by Br, or cyclohexylene, $R^7$ and $R^{10}$ are the same or different, each of which denotes methylene, $C(CH_3)_2$, or S, and m denotes an integer of 1 to 40). The compounds represented by general formula (III) in which $R^6$, $R^8$, $R^9$, and $R^{11}$ are the same, and $R^7$ and $R^{10}$ are the same can be more preferably used. The compounds in which $R^6$, $R^8$, $R^9$, and $R^{11}$ are phenylene, and $R^7$ and $R^{10}$ are methylene, the compounds in which $R^6$, $R^8$, $R^9$, and $R^{11}$ are cyclohexylene, and $R^7$ and $R^{10}$ are $C(CH_3)_2$, or the compounds in which $R^6$, $R^8$, $R^9$, and $R^{11}$ are cyclohexylene, and $R^7$ and $R^{10}$ are methylene can be even more preferably used.

Examples of the dithiocarbonate compound derived from an alcohol are compounds obtained by preparing a glycidyl ether by allowing an alcohol, such as methanol, ethanol, propanol, butanol, octanol, nonanol, isodecanol, ethylene glycol, propylene glycol, neopentyl glycol, glycerin, trimethylolpropane, pentaerythritol, dipentaerythritol, butylethylpropandiol, and 2,4-diethyl-3-methyl-1,5-pentandiol, to react with epichlorohydrin, and then allowing the glycidyl ether to react with carbon disulfide.

Examples of the dithiocarbonate compound derived from a carboxylic acid are compounds obtained by preparing a glycidyl compound by allowing a carboxylic acid, such as acetic acid, propionic acid, butyric acid, stearic acid, adipic acid, and phthalic acid, to react with epichlorohydrin, and then allowing the glycidyl compound to react with carbon disulfide.

A compound having at least one 5-membered ring dithiocarbonate group can be obtained by allowing an oxirane compound, which corresponds to the intended product, and carbon disulfide to react in the presence of alkali halide such as lithium bromide in accordance with a known method (Japanese Unexamined Patent Application, First Publication No. Hei 5-257027 or the Journal of Organic Chemistry (J. Org. Chem.), 60, 473 (1995)).

For example, a hydroxy compound represented by general formula (III) can be obtained by allowing a commercially available epoxy resin ("E-1001~1007", manufactured by Yuka Shell Epoxy Kabushiki Kaisha), which corresponds to the hydroxy compound, and carbon disulfide to react in the presence of alkali halide such as lithium bromide. Although a commercially available oxirane compound may be used, an oxirane compound may be obtained by allowing a compound having a hydroxyl group and epichlorohydrin to react in the presence of a base, if the oxirane compound is not commercially available.

A ketimine derivative, an enamine derivative, or an aldimine derivative, which is a component of a composition according to the present invention, can be synthesized from an amino compound having a primary or secondary amino group and a lower molecular carbonyl compound or a lower molecular aldehyde compound in accordance with a known method. However, a commercially available product such as "H-2" manufactured by Yuka Shell Epoxy Kabushiki Kaisha, for example, may also be used.

As the amino compound, a primary or secondary amine compound can be used.

Examples of such amino compounds are lower molecular amino compounds including monoamines such as methylamine, ethylamine, propylamine, butylamine, hexylamine, octylamine, monoethanolamine, diethanolamine, dimethylamine, diethylamine, diisopropylamine, dibutylamine, and 2-amino-2-methylpropanol; diamines such as ethylenediamine, 1,2-diaminopropane, 1,3-diaminopropane, 1,4-diaminobutane, 1,6-diaminohexane, 1,8-diaminooctane, 1,2-diaminocyclohexane, dimer acid amide, N,N'-bis(2-aminoethyl)ethylenediamine, N,N'-bis(3-aminopropyl)ethylenediamine, and N,N'-dimethyldiaminopropane; triamines such as dicyandiamide, 1,2,3-triaminopropane, 1,2,3-triamino-2-methylpropane, 1,3-diamino-2-aminomethylpropane, 1,2-diamino-2-aminomethylbutane, 1,3-diamino-2-methyl-2-aminomethylpropane, tris(2-aminoethyl)ethane, tris(6-aminohexyl) isocyanurate, 1,3-diamino-2-methylaminopropane, 2-amino-1,3-bis(isopropylamino)-2-methylpropane, and 2-amino-1-isopropylamino-2-isopropylaminomethylbutane; tetramines such as tetrakis(aminomethyl)methane, tetrakis(methylaminomethyl)methane, tetrakis(2-aminoethylaminomethyl)methane, and 1,1,1-tris(2-aminoethylaminomethyl)ethane; polyalkylene polyamines such as diethylenetriamine, triethylenetetramine, tetraethylenepentamine, hexaethyleneoctamine, nonaethylenedecamine, 1,3-bis(2-aminoethylamino)propane, triethylene-bis(trimethylene)hexamine, bis(3-aminopropyl)amine, 1,3-bis(3-aminopropylamino)propane, spermidine, homospermidine, N-(4-aminobutyl)cadaverine, bis(5-aminopentyl)amine, spermine, 1,6-bis(2-aminoethylamino)hexane, and 1,10-bis(2-aminoethylamino)decane; alicyclic amines such as pyrrolidine, piperidine, piperazine, morpholine, and thiomorpholine; basic amino acids such as lysine, ornithine, and arginine; aromatic amines such as aniline and diphenylamine; arakylamines such as benzylamine; and basic nitrogen-containing heterocyclic compounds such as pyrrole, imidazole, and triazole.

Higher molecular compounds including copolymers of a vinyl polymerizable monomer having an amino group in its molecule, such as monohydrazide (meth)acrylate, 2-aminoethyl (meth)acrylate, allylamine, N-methylallylamine, and diallylamine, with another vinyl polymerizable monomer; hydrolysates of a copolymer of N-vinylformamide or N-vinylacetamide with another vinyl monomer; and polyamine addition products of an epoxy compound may also be used.

Examples of lower molecular carbonyl compounds for synthesizing the ketimine derivative or the enamine derivative are ketone compounds such as acetone, methyl ethyl ketone, methyl isobutyl ketone, diisobutyl ketone, and cyclohexanone.

Examples of lower molecular carbonyl compounds for synthesizing aldimine derivatives are aldehyde compounds such as acetaldehyde, propionaldehyde, isobutyraldehyde, octylaldehyde, benzaldehyde, α-tolualdehyde, 4-ethylbenzaldehyde, 4-propylbenzaldehyde, 4-butylbenzaldehyde, 2,4-dimethylbenzaldehyde, 2,4,5-trimethylbenzaldehyde, p-anisaldehyde, and p-ethoxybenzaldehyde.

The lower carbonyl compound is normally used in an amount of 0.5 to 5 equivalents, or preferably 0.8 to 1.5 equivalents, to the amino compound. However, use of a greatly excessive amount of the lower carbonyl compound is not objected to, since it can also serve as a solvent.

The composition according to the present invention in which the ketimine derivative, the enamine derivative, or the aldimine derivative is used in such an amount that the following value is 0.3 to 2.0, or particularly 0.8 to 1.2, imparts good properties to a coating.

Amino or imino groups in which a hydrogen may be substituted by alkyl or the like 5-membered ring dithiocarbonate group The composition according to the present invention is characterized by comprising a polymer or a compound having at least one dithiocarbonate group, and a ketimine derivative, an enamine derivative, or an aldimine derivative, and can be obtained by dispersing these components into each other and mixing them; however, one of various solvents may be incorporated, if necessary. In this case, as the solvent, one of the above polymerization solvents or a mixture of two to four of them may be used in a 0.2- to 100-fold amount (by weight) of the copolymer for the present invention.

The composition according to the present invention is useful in a coating, an adhesive, an ink, a sealing agent, a sealant, or the like In particular, the composition is useful in a solvent-based coating, which comprises a polymer or a compound having at least one dithiocarbonate group, and a ketimine derivative, an enamine derivative, or an aldimine derivative, and a solvent other than water, in view of storage stability. Here, as the "solvent other than water", the above polymerization solvents other than water, for example, can be used.

Since the composition according to the present invention possesses superior storage stability, the composition can be used as a one-liquid type composition for use in a coating or the like.

In addition, the curing reaction time of the composition according to the present invention can be controlled by selecting conditions such as the type of ketimine derivative, enamine derivative, or aldimine derivative in the composition.

A solution or suspension of the composition according to the present invention can be used by itself as a clear coating of clear ink, but it can also be used as a colored coating or a colored ink, with a pigment or a dipersed pigment further added. In the process of dispersing the pigment, a conventional paint shaker, ball mill, or the like can be used.

With the composition according to the present invention, various ultraviolet absorbers, antioxidants, hindered amine light stabilizers, pigment dispersants, or the like may be incorporated, if necessary. The composition according to the present invention may comprise various conventionally used alkyd resins, acrylic resins, cellulosic resins, petroleum resins, epoxy resins, plasticizers, film-forming auxiliaries, water absorbent, or the like.

When the composition according to the present invention is used in a coating, a coating process such as conventional brush coating, spray coating, or the like may be employed, and the curing conditions may be selected from a wide range from normal temperature drying to heat drying. The type of article to which the composition is applied can be metal, wood, plastic, inorganic materials, concrete, asphalt, or the like. The composition is useful as an under coat, a top coat, or a one-coat finishing for protecting the material and improving the appearance.

Embodiments of the present invention will be described by working examples and reference examples.

BEST MODE FOR CARRYING OUT THE INVENTION

REFERENCE EXAMPLE 1

(Resin: A-1)

A flask equipped with a dropping device, a stirrer, a thermometer, a condenser, and a nitrogen gas introduction tube was charged with 150 g of methyl isobutyl ketone. The flask was heated to 100° C., and then purged with nitrogen. Subsequently, a liquid mixture of 30 g of 5-(methacryloyl) methyl-1,3-oxathiolane-2-thione, 118.5 g of butyl methacrylate, and 1.5 g of t-butyl peroxy-2-ethylhexanoate, which is a polymerization catalyst, was added dropwise into the flask over 3 hours. The polymerization was completed after maturation at 100° C. for 3 hours to yield a resin possessing a solid content of 50% by weight and a weight-average molecular weight of 81,000 (resin: A-1). The weight-average molecular weight was analyzed by gel permeation chromatography (GPC) in accordance with the following method. In addition, weight-average molecular weights in the following reference examples were measured by a similar method.

(Conditions of GPC Analysis)

Column: HXL-L, GMHXL, G-4000HXL, and G-2000HXL (manufactured by Tosoh Corporation) connected serially Column retention temperature: 40° C.

Detector: RI

Developing solvent: Tetrahydrofuran
(flow rate: 1 ml/min)

REFERENCE EXAMPLE 2

(Resin: A-2)

A flask equipped with a dropping device, a stirrer, a thermometer, a condenser, and a nitrogen gas introduction tube was charged with 150 g of methyl isobutyl ketone. The flask was heated to 100° C., and then purged with nitrogen. Subsequently, a liquid mixture of 19.6 g of glycidyl methacrylate, 128.9 g of butyl methacrylate, and 1.5 g of t-butyl peroxy-2-hexanoate was added dropwise into the flask over 3 hours. The polymerization was completed after maturation at 100° C. for 3 hours to yield a resin having a solid content of 50% by weight and a weight-average molecular weight of 22,000 (resin: A-2).

REFERENCE EXAMPLE 3

(Resin: A-1)

A 10-L flask equipped with devices similar to those used in Reference Example 1 was charged with 5 L of tetrahydrofuran, 500 g of bisphenol A-epichlorohydrin type epoxy resin ("E-1001", manufactured by Yuka Shell Epoxy Kabushiki Kaisha), and 25 g of lithium bromide, which were stirred well. Then, 340 mL of carbon disulfide was added dropwise to the solution in such a manner that the temperature of the solution reaches 25° C., and thereafter the flask was heated to 45° C., and the reaction was allowed to proceed for 8 hours.

After the reaction, the reaction liquid was concentrated under reduced pressure. To the concentrated residue obtained, 5 L of chloroform and 3 L of water was added, and separation of the liquid was performed. To the organic phase which was taken out, 500 L of saturated saline solution was added, and separation of the liquid was performed again. The organic phase obtained was dehydrated using 300 g of magnesium sulfate, and thereafter chloroform was removed by distillation to yield 445 g of crude product. A resin (resin: A-3) was obtained by purifying 400 g of the crude product by silica gel column chromatography (developing solvent: chloroform/acetone=20/1). NMR and IR analytical data on the purified product obtained are shown below. $^1$H-NMR (CDCl$_3$, δ ppm, 400 MHz): 1.63 (s, 18H), 2.52 (d, J=5.1 Hz, 2H), 3.73 (dd, J=7.1, 12.0 Hz, 2H), 3.78 (dd, J=7.6, 8.0 HZ, 2H), 4.10 (dd, J=5.6, 12.0 Hz, 4H), 4.13 (dd, J=4.6, 8.0 Hz, 4H), 4.25 (dd, J=5.6, 10.3 Hz, 2H), 4.30 (dd, J=5.6, 10.3 Hz, 2H), 4.35 (q, J=5.4 Hz, 2H), 5.42 (m, 2H), 6.81 (dd, J=1.7, 8.8 Hz, 6H), 6.83 (dd, J=2.0, 8.8 Hz, 6H), 7.13 (dd, J=1.5, 8.0 Hz, 12H) IR (NaCl, cm$^{-1}$): 508, 1184, 1241, 1606, 3037, 3442.

REFERENCE EXAMPLE 4

(Resin: A-4)

A flask equipped with a stirrer, a thermometer, a nitrogen gas introduction tube, and a dropping funnel was charged with 200 g of butyl cellosolve, and heated to 100° C. A liquid mixture of 60 g of (methacryloyloxy)methyl-1,3-oxathiolane-2-thione, 26 g of acryllic acid, 294 g of butyl methacrylate, and 20 g of 2,2-azobis-2-methylbutyronitrile was added dropwise from the dropping funnel into the flask over 3 hours. After completion of the dropwise addition, maturation was allowed to take place for 3 hours at the same temperature. After cooling, 32 g of triethylamine and 35 g of water were added to yield the intended resin (resin: A-4). The resin solution obtained had a solid content of 60% by weight and a weight-average molecular weight of 10,000 (resin: A-4).

REFERENCE EXAMPLE 5

Synthesis of Aldimine Derivative

A flask equipped with a dropping device, a stirrer, a thermometer, a condenser, and a nitrogen gas introduction tube was charged with 20 g of tetrahydrofuran and 10 g of 1,3-diaminopropane. The flask was maintained at 5° C. When the temperature became stable, 23.4 g of n-butyraldehyde was added dropwise into the flask over 1 hour. After completion of the dropwise addition, the reaction was allowed to proceed at the same temperature for 5 hours.

The reacted solution obtained was concentrated at 50° C., and when the amount stayed constant, the concentrating process was stopped to yield an aldimine derivative. FT-IR measurement performed on the reaction product obtained resulted in showing the characteristic absorption of —N=CH— at 1640 $cm^{-1}$.

REFERENCE EXAMPLE 6

Synthesis of Ketimine Derivative

A flask equipped with a stirrer, a thermometer, a condenser, a dropping funnel, and a nitrogen gas introduction tube was charged with 250 g of methyl isobutyl ketone and 58 g of 1,6-diaminohexane. The flask was heated to 120° C. While water produced at this temperature was occasionally removed under reflux, the reaction was allowed to proceed for 3 hours. The reacted solution obtained was concentrated at 50° C., and when the amount stayed constant, the concentrating process was stopped to yield a ketimine derivative. FT-IR measurement performed on the reaction product obtained resulted in showing the characteristic absorption of —N=CH— at 1640 $cm^{-1}$.

WORKING EXAMPLE 1

A clear varnish was prepared by adding 0.51 g of a ketimine compound manufactured by Yuka Shell Epoxy Kabushiki Kaisha (trade name: H-2; manufactured by Yuka Shell Epoxy Kabushiki Kaisha) to 20 g of resin (A-1) obtained by Reference Example 1, and stirring them.

WORKING EXAMPLE 2

A clear varnish was prepared by adding 0.45 g of the aldimine derivative obtained by Reference Example 5 to 20 g of resin (A-1) obtained by Reference Example 1, and stirring them.

WORKING EXAMPLE 3

A clear varnish was prepared by adding 0.32 g of the ketimine derivative obtained by Reference Example 5 to 20 g of resin (A-1) obtained by Reference Example 1, and stirring them.

WORKING EXAMPLE 4

A clear varnish was prepared by adding 12.0 g of a ketimine compound manufactured by Yuka Shell Epoxy Kabushiki Kaisha (trade name: H-2; manufactured by Yuka Shell Epoxy Kabushiki Kaisha) to 100 g of resin (A-4) obtained by Reference Example 4, and stirring them.

COMPARATIVE EXAMPLE 1

A clear varnish was prepared by adding 0.34 g of 1,3-diaminopropane to 20 g of resin (A-1) obtained by Reference Example 1, and stirring them.

COMPARATIVE EXAMPLE 2

A clear varnish was prepared by adding 0.20 g of 1,6-diaminohexane to 20 g of resin (A-1) obtained by Reference Example 1, and stirring them.

COMPARATIVE EXAMPLE 3

A clear varnish was prepared by adding 0.51 g of a ketimine compound manufactured by Yuka Shell Epoxy Kabushiki Kaisha (trade name: H-2; manufactured by Yuka Shell Epoxy Kabushiki Kaisha) to 20 g of resin (A-2) obtained by Reference Example 2, and stirring them.

WORKING EXAMPLE 5

A clear varnish was prepared by adding 0.53 g of a ketimine compound (trade name: H-2; manufactured by Yuka Shell Epoxy Kabushiki Kaisha) to 10 g of resin (A-3) obtained by Reference Example 3, and stirring them.

COMPARATIVE EXAMPLE 4

A clear varnish was prepared by adding 0.35 g of 1,3-diaminopropane to 10 g of resin (A-3) obtained by Reference Example 3, and stirring them.

COMPARATIVE EXAMPLE 5

A clear varnish was prepared by dissolving 5 g of an epoxy resin manufactured by Yuka Shell Epoxy Kabushiki Kaisha ("E-1001") in 5 g of methyl isobutyl ketone, thereafter adding 0.62 g of a ketimine compound (trade name: H-2; manufactured by Yuka Shell Epoxy Kabushiki Kaisha) to the solution, and stirring them.

TEST EXAMPLE 1

Test pieces were prepared by applying clear varnishes obtained by Working Examples 1 to 4 and Comparative Examples 1 to 4 to cold-finished steel plates (manufactured by Japan Test Panel), which were treated with iron phosphate, using an applicator coater so that the thickness of the films after drying would be 30 μm, and drying them at room temperature for a week. The following tests were conducted on the test pieces.

TABLE 1

|  | Working Example 1 | Working Example 2 | Working Example 3 | Working Example 4 | Comparative Example 1 | Comparative Example 2 | Comparative Example 3 |
|---|---|---|---|---|---|---|---|
| Gel fraction | 89.1% | 65.0% | 94.0% | 80.0% | Not measurable | Not measurable | 0.4% |
| Coating appearance | No abnormality | No abnormality | No abnormality | Not inspected | — | — | No abnormality |
| Film thickness (μm) | 28 | 30 | 30 | Not measured | — | — | 28 |
| Pencil Hardness | B | 2B | H | Not measured | — | — | <4B |
| Adhesion | 100/100 | 100/100 | 100/100 | Not measured | — | — | 0/100 |
| Impact Resistance (cm) | 25 | 15 | 25 | Not measured | — | — | <5 |
| MEK resistance (No. of times) | 100 | 70 | 100 | 80 | — | — | 5 |
| Water resistance | No abnormality | No abnormality | No abnormality | Not inspected | — | — | Whitened |
| Storage Stability | Not thickened | Not thickened | Not thickened | Not inspected | Gelated | Gelated | Not thickened |

Gel fraction: About 0.5 g of the film was collected from a test piece, and cleaned by a Soxhlet extractor under acetone reflux for 8 hours. Then, drying under reduced pressure was performed overnight, and the remaining rate by weight was determined, and was taken as the gel fraction.

Pencil hardness: Tests were conducted by the manual scratch method according to JIS K5400 (General Test Method for Coatings).

Adhesion: Tests were conducted by the cross-cut adhesion test method according to JIS K5400 (General Test Method for Coatings).

Impact resistance: Tests were conducted by dropping a 500-g weight on a test piece, and measuring the height required to cause peeling of the coating film, using a Du Pont impact tester according to JIS K5400 (General Test Method for Coatings).

MEK resistance: A cloth was soaked with methyl ethyl ketone (MEK), and tests were conducted by rubbing a test piece back and forth with the cloth under a load of 500 g. The number of rubbing strokes was counted until the article coated became exposed.

Water resistance: The appearance of a test piece after it was immersed in water at room temperature for 120 hours was visually inspected according to JIS K5400 (General Test Method for Coatings).

Storage stability: A coating was kept in a sealed glass container in a thermostat at 40° C. for 1 month, and then the appearance and flowability of the coating were visually inspected.

The results of the evaluation tests are shown in Tables 1 and 2.

TABLE 2

|  | Working Example 5 | Comparative Example 4 | Comparative Example 5 |
|---|---|---|---|
| Gel fraction | 78.7% | 88.4% | 55.3% |
| Storage Stability | Not thickened | Gelated in 10 minutes | Not thickened |

Tables 1 and 2 show that the compositions of the present invention are superior in coating properties and storage stability to the compositions of Comparative Examples.

INDUSTRIAL APPLICABILITY

According to the present invention, dithiocarbonate compositions which are useful in coatings, adhesives, inks, sealing agents, sealants, and the like, are provided.

What is claimed is:
1. A composition, comprising:

(i) a polymer or a compound having at least one 5-membered ring dithiocarbonate group represented by general formula (I):

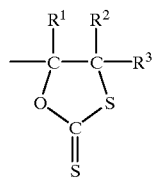

(I)

wherein $R^1$, $R^2$, and $R^3$ independently denote hydrogen or a lower alkyl), and (ii) a ketimine derivative having a structure represented by formula (A),

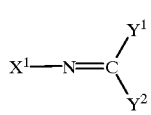

(A)

(wherein $X^1$, $Y^1$, and $Y^2$ are independently groups other than hydrogen), an enamine derivative having a structure represented by formula (B)

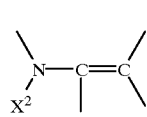

(B)

(wherein $X^2$ is a group other than hydrogen), or an aldimine derivative having a structure represented by general formula (C)

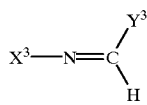

(C)

(wherein $X^3$ and $Y^3$ are independent groups other than hydrogen).

2. A composition according to claim 1, wherein the ketimine derivative, the enamine derivative, or the aldimine derivative is a compound obtained by the reaction of:

(A) an amino compound selected from the group consisting of methylamine, ethylamine, propylamine, butylamine, hexylamine, octylamine, monoethanolamine, diethanolamine, dimethylamine, diethylamine, diisopropylamine, dibutylamine, 2-amino-2-methylpropanol, ethylenediamine, 1,2-diaminopropane, 1,3-diaminopropane, 1,4-diaminobutane, 1,6-diaminohexane, 1,8-diaminooctane, 1,2-diaminocyclohexane, dimer acid amide, N,N' bis(2-aminoethyl)ethylenediamine, N,N'-bis (3-aminopropyl) ethylenediamine, N,N'-dimethyldiamninopropane, dicyandiamide, 1,2,3-triaminopropane, 1,2,3-triamino-2-methylpropane, 1,3-diamino-2-aminomethylpropane, 1,2-diamino-2-aminoethylbutane, 1,3-diamino-2-methyl-2-aminomethylpropane, tris(2-aminoethyl)ethane, tris(6-aminohexyl) isocyanurate, 1,3-diamino-2-methylaminopropane, 2-amino-1,3-bis (isopropylamino)-2-methylpropane, 2-amino-1-isopropylamino-2-isopropylaminomethylbutane, tetrakis (aminomethyl) methane, tetrakis (methylaminomethyl)methane, tetrakis(2-aminoethylaminomethyl)methane, 1,1,1-tris(2-aminoethylaminoethyl) ethane, diethylenetriamine, triethylenetetramine, tetraethylenepentamine, hexaethyleneoctamine, nonaethylenedecamine, 1,3-bis (2-aminoethylamino) propane, triethylene-bis (trimethylene) hexamine, bis(3-aminopropyl)amine, 1,3-bis(3-aminopropylamino)propane, spermidine, homospermidine, N-(4-aminobutyl)cadaverine, bis(5-aminopentyl)amine, spermine, 1,6-bis-(2-aminoethylamino)hexane, 1,10-bis(2-aminoethylamino)decane, pyrrolidine, piperidine, piperazine, morpholine, thiomorpholine, lysine, ornithine, arginine, aniline or diphenylamine, benzylamine, pyrrole, imidazole, triazole, a copolymer of (monohydrazide (meth)acrylate, 2-aminoethyl (meth)acrylate, allylamine, N-methylallylamine, or diallylamine) with another vinyl polymerizable monomer, a hydrolysate of a copolymer of N-vinylformamide with another vinyl monomer, a hydrosylate of a copolymer of N-vinylacetamide with another vinyl monomer, and a hydrosylate of a copolymer of N-vinylacetamide with another vinyl monomer, and a polyamine addition product of an epoxy compound, and (B) a carbonyl compound selected from the group consisting of acetone, methyl ethyl ketone, methyl isobutyl ketone, diisobutyl ketone, cyclohexanone, acetaldehyde, propionaldehyde, isobutyraldehyde, octylaldehyde, benzaldehyde, α-tetualdehyde, 4-ethylbenzaldehyde, 4-propylbenzaldehyde, 4-butylbenzaldehyde, 2,4-dimethylbenzaldehyde, 2,4,5-trimethylbenzaldehyde, p-anisaldehyde, and p-ethoxybenzaldehyde.

3. A composition according to claim 1, wherein the polymer having at least one 5-membered ring dithiocarbonate group is a copolymer.

4. A composition according to claim 3, wherein the copolymer is a vinyl copolymer.

5. A composition according to claim 4, wherein the vinyl copolymer contains a structural unit represented by general formula (II)

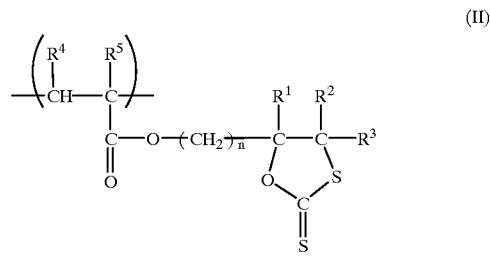

(II)

(wherein, in the formula, the definitions of $R^1$, $R^2$, and $R^3$ are the same as those above, $R^4$ and $R^5$ are the same or different, each of which denotes hydrogen, methyl, or ethyl, and n denotes an integer of 1 to 4).

6. A composition according to claim 5, wherein the vinyl copolymer is a copolymer of acrylic acid or methacrylic acid or a lower alkyl ester thereof.

7. A composition comprising (i) a compound having at least one 5-membered ring dithiocarbonate group represented by general formula (I):

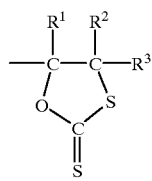

wherein R¹, R², and R³ independently denote hydrogen or a lower alkyl, and (ii) a ketimine derivative, an enamine derivative, or an aldimine derivative,
wherein the compound having at least one 5-membered ring dithiocarbonate group is represented by formula (III):

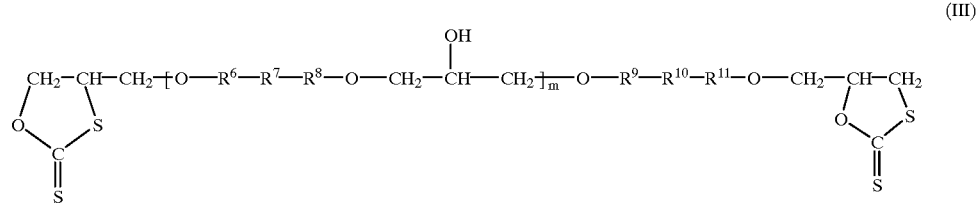

wherein $R^6$, $R^8$, $R^9$ and $R^{11}$ independently denote a phenylene in which 1 to 4 hydrogen atoms may be substituted by Br, or cyclohexylene; $R^7$ and $R^{10}$ independently denote methylene, $C(CH_3)_2$, or S; and m denotes an integer of 1 to 40.

8. A coating comprising a composition of any of claims 1–7.

9. A solvent coating comprising a solvent other than water and a composition of any of claims 1–7.

10. A composition according to any of claims 1–7, which contains a solvent.

11. A composition, comprising:
(i) a polymer or a compound having at least one 5-membered ring dithiocarbonate group represented by general formula (I):

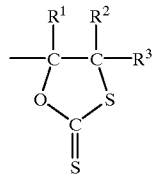

wherein R¹, R², and R³ independently denote hydrogen or a lower alkyl, and
(ii) a compound obtained from a reaction between an amino compound, and a ketone compound or an aldehyde compound.

12. A composition according to claim 7, wherein the ketimine derivative, the enamine derivative, or the aldimine derivative is a compound obtained by the reaction of:

(A) an amino compound selected from the group consisting of methylamine, ethylamine, propylamine, butylamine, hexylamine, octylamine, monoethanolamine, diethanolamine, dimethylamine, diethylamine, diisopropylamine, dibutylamine, 2-amino-2-methylpropanol, ethylenediamine, 1,2-diaminopropane, 1,3-diaminopropane, 1,4-diaminobutane, 1,6-diaminohexane, 1,8-diaminooctane, 1,2-diaminocyclohexane, dimer acid amide, N,N' bis(2-aminoethyl)ethylenediamine, N,N'-bis (3-aminopropyl) ethylenediamine, N,N'-dimethyldiaminopropane, dicyandiamide, 1,2,3-triaminopropane, 1,2,3-triamino-2-methylpropane, 1,3-diamino-2-aminomethylpropane, 1,2-diamino-2-aminoethylbutane, 1,3-diamino-2-methyl-2-aminomethylpropane, tris(2-aminoethyl)ethane, tris(6-aminohexyl) isocyanurate, 1,3-diamino-2-methylaminopropane, 2-amino-1,3-bis(isopropylamino)-2-methylpropane, 2-amino-1-isopropylamino-2-isopropylaminomethylbutane, tetrakis (aminomethyl) methane, tetrakis (methylaminomethyl)methane, tetrakis(2-aminoethylaminomethyl)methane, 1,1,1-tris(2-aminoethylaminoethyl) ethane, diethylenetriamine, triethylenetetramine, tetraethylenepentamine, hexaethyleneoctamine, nonaethylenedecamine, 1,3-bis (2-aminoethylamino) propane, triethylene-bis (trimethylene) hexamine, bis(3-aminopropyl)amine, 1,3-bis(3-aminopropylamino)propane, spermidine, homospermidine, N-(4-aminobutyl)cadaverine, bis(5-aminopentyl)amine, spermine, 1,6-bis-(2-aminoethylamino)hexane, 1,10-bis(2-aminoethylamino)decane, pyrrolidine, piperidine, piperazine, morpholine, thiomorpholine, lysine, omithine, arginine, aniline or diphenylamine, benzylamine, pyrrole, imidazole, triazole, a copolymer of a vinyl polymerizable monomer having an amino group in its molecule, which is (monohydrazide (meth) acrylate, 2-aminoethyl (meth)acrylate, allylamine, N-methylallylamine, or diallylamine) with another vinyl polymerizable monomer, a hydrolysate of a copolymer of N-vinylformamide with another vinyl monomer, a hydrosylate of a copolymer of N-vinylacetamide with another vinyl monomer, and a polyamine addition product of an epoxy compound, and (B) a carbonyl compound selected from the group consisting of acetone, methyl ethyl ketone, methyl isobutyl ketone, diisobutyl ketone, cyclohexanone, acetaldehyde, propionaldehyde, isobutyraldehyde, octylaldehyde, benzaldehyde, α-tetualdehyde, 4-ethylbenzaldehyde, 4-propylbenzaldehyde, 4-butylbenzaldehyde, 2,4-dimethylbenzaldehyde, 2,4,5-trimethylbenzaldehyde, p-anisaldehyde, and p-ethoxybenzaldehyde.

\* \* \* \* \*

UNITED STATES PATENT AND TRADEMARK OFFICE
CERTIFICATE OF CORRECTION

PATENT NO. : 6,372,871 B1
DATED : April 16, 2002
INVENTOR(S) : Shinichiro Jimbo et al.

It is certified that error appears in the above-identified patent and that said Letters Patent is hereby corrected as shown below:

Title page,
Foreign Application Priority Data
"Apr. 12, 1996" should read -- Dec. 4, 1996 --.

Column 1,
Line 28, "polymerization;" should read -- polymerization, --.

Column 5,
Line 7, "used" should read -- used. --; and
Line 66, "adivance," should read -- advance, --.

Column 8,
Line 50, "5-membered" should read -- ¶ 5-membered --; and
Line 67, "like" should read -- like. --.

Column 10,
Line 58, "H-NMR" should read -- ¶'H-NMR --; and
Line 60, "8.0 HZ, " should read -- 8.0 Hz, --.

Column 15,
Line 11, "wherein" should read -- (wherein --; and
Line 60, "dimethyldiamninopropane," should read -- dimethyldiaminopropane, --.

Column 16,
Line 31, "α-tetudldehyde," should read -- α-tetraldehyde, --; and
Line 65, "comprising" should read -- comprising: --.

Column 17,
Lines 36 and 38, "1-7." should read -- 1-7, 11 or 12. --; and
Line 39, "1-7," should read -- 1-7, 11 or 12, --.

UNITED STATES PATENT AND TRADEMARK OFFICE
CERTIFICATE OF CORRECTION

PATENT NO. : 6,372,871 B1
DATED : April 16, 2002
INVENTOR(S) : Shinichiro Jimbo et al.

It is certified that error appears in the above-identified patent and that said Letters Patent is hereby corrected as shown below:

Column 18,
Line 44, "omithine," should read -- ornithine, --; and
Line 60, "α-tetudldehyde," should read -- α-tetraldehyde, --.

Signed and Sealed this

Twenty-ninth Day of October, 2002

*Attest:*

*Attesting Officer*

JAMES E. ROGAN
*Director of the United States Patent and Trademark Office*